(12) United States Patent
Orte et al.

(10) Patent No.: US 10,351,588 B2
(45) Date of Patent: Jul. 16, 2019

(54) PRODUCTION OF STEROLS

(71) Applicant: FORCHEM OYJ, Rauma (FI)

(72) Inventors: Juha Orte, Rauma (FI); Mikko Rintola, Rauma (FI)

(73) Assignee: FORCHEM OYJ, Rauma (FI)

( * ) Notice: Subject to any disclaimer, the term of this patent is extended or adjusted under 35 U.S.C. 154(b) by 0 days.

(21) Appl. No.: 15/576,431

(22) PCT Filed: May 24, 2016

(86) PCT No.: PCT/FI2016/050353
§ 371 (c)(1),
(2) Date: Nov. 22, 2017

(87) PCT Pub. No.: WO2016/189200
PCT Pub. Date: Dec. 1, 2016

(65) Prior Publication Data
US 2018/0155387 A1 Jun. 7, 2018

(30) Foreign Application Priority Data
May 25, 2015 (FI) ...................................... 20155387

(51) Int. Cl.
| | | |
|---|---|---|
| *C07J 9/00* | (2006.01) | |
| *C07C 67/03* | (2006.01) | |
| *C11B 13/00* | (2006.01) | |
| *C11C 3/00* | (2006.01) | |

(52) U.S. Cl.
CPC ................. *C07J 9/00* (2013.01); *C07C 67/03* (2013.01); *C11B 13/005* (2013.01); *C11C 3/003* (2013.01); *Y02W 30/74* (2015.05)

(58) Field of Classification Search
CPC ........... C11C 3/003; C07C 67/03; C07J 9/00; Y02W 30/74
See application file for complete search history.

(56) References Cited

U.S. PATENT DOCUMENTS

2013/0041192 A1  2/2013  Saviainen et al.

FOREIGN PATENT DOCUMENTS

| CN | 102796619 A | 11/2012 | |
|---|---|---|---|
| DE | 3313915 A1 | 10/1984 | |
| EP | 1 081 156 A2 | 3/2001 | |
| EP | 1 291 355 A1 | 3/2003 | |
| EP | 1291355 A1 * | 3/2003 | ............... C07J 9/00 |
| WO | WO 2004/074233 A1 | 9/2004 | |
| WO | WO 2009/113935 A1 | 9/2009 | |
| WO | WO 2011/117474 A1 | 9/2011 | |

OTHER PUBLICATIONS

International Search Report, issued in PCT/FI2018/050353 (PCT/ISA/210), dated Aug. 19, 2016.
Search Report issued in Finland priority of application 20155387, dated Jan. 28, 2016.
Written Opinion of the International Searching Authority, issued in PCT/FI2016/050353 (PCT/ISA/237), dated Aug. 19, 2016.
Cantrill, Ph.D. et al., "Phytosterols, Phytostanols and Their Esters: Chemical and Technical Assessment," Jan. 1, 2008, pp. 1-13, URL: http://www.fao.org/fileadmin/templates/agns/pdf/jecfa/cta/69/Phytosterols.pdf.
European Patent Office Communication and extended search report issued in the corresponding European Patent Application No. 16799414.4 dated Nov. 12, 2018.
Fernandes et al., "Phytosterols: Applications and recovery methods," Bioresource Technology, vol. 98, No. 12, Mar. 19, 2007, pp. 2335-2350.

* cited by examiner

Primary Examiner — Paul A Zucker
(74) Attorney, Agent, or Firm — Birch, Stewart, Kolasch & Birch, LLP

(57) ABSTRACT

Method of recovering sterols from tall oil pitch which contains steryl esters. In the method the tall oil pitch is subjected to a transefterification reaction with a lower alcohol in a reaction zone to provide a reaction product mixture containing lower alkyl fatty acid esters, free sterols, and at least some unreacted steryl esters. The invention comprises separating the transesterified esters from the reaction product mixture to form a sterol rich fraction which contains free sterols and unreacted steryl esters, liberating sterols from the unreacted steryl esters to form further free sterols, and recovering and optionally purifying the free sterols. The recovery of free sterols can be increased to up to 80 wt % or more while avoiding the formation of undesired side streams containing troublesome impurities.

36 Claims, 2 Drawing Sheets

PRODUCTION OF STEROLS

FIELD OF INVENTION

The present invention relates to the production of sterols. In particular the present invention concerns a method of producing sterols from tall oil pitch. The present invention also concerns joint production of lower alkyl esters of fatty acids and sterols from tall oil pitch.

BACKGROUND ART

Sterols are alcoholic substances found in non-saponifiable matter of plants. They are valuable compounds which can be used in the food, in the pharmaceuticals and in the chemical industries.

Sterols can be recovered from tall oil pitch which is a distillation residue obtained from crude tall oil distillation. Crude tall oil (CTO) originates from the black liquor obtained from coniferous trees by extraction in a kraft pulp process. CTO is typically recovered from soap skimming of black liquor and contains high quantities of fatty acid sodium salts, resin acid sodium salts and unsaponifiables and neutral substances which include fatty alcohols, free sterols, steryl esters, and fatty acid esters.

In kraft pulp mills, skimmed soap is collected and acidulated with a mineral acid, such as sulphuric acid, to obtain an oil phase and a water phase. The oil phase, i.e. the crude tall oil, contains free fatty acids, resin acids and unsaponifiables where the amount of unsaponifiables can range from 10 to 35% by weight depending on the species and a quality of coniferous trees used. Crude tall oil is typically dried and distillated at high temperatures under vacuum to yield a light phase, a rosin phase, a fatty acid phase and a pitch phase.

The composition of the tall oil pitch is strongly dependent on the distillation equipment and operating conditions employed in the distillation of tall oil. The residual pitch fraction contains various quantities of fatty and rosin acids and a substantial amount of the original unsaponifiables and neutral substances with concentrated amounts of sterols and steryl esters.

Typically, sterols are obtained from the raw-material by processing methods which comprise a first step of modifying steryl esters and generating free sterols which are then further concentrated into a sterol rich fraction before it is isolated from its impurities to obtain pure sterols.

It is known in the art that sterols can be effectively separated from tall oil pitch by modifying steryl esters in ways which liberate free sterol and fatty acid forms from esterified sterols. Processes are known in the art for saponification of tall oil pitch with an alkali to hydrolyze the fatty acid steryl esters and to release sterols and convert fatty acid to corresponding salts. Sterols are further processed to obtain purified sterols.

Free sterols and fatty acids can be obtained by hydrolyzing reactions. These components can then be separated.

The sterols obtained by the known methods are concentrated by using consecutive evaporations or distillations. The concentration steps commonly comprise evaporation separations carried out in evaporation units, preferably by using technologies in art based on continuous film generating evaporators like Falling Film Evaporator (FFE), Wiped Film Evaporator (WFE), Thin Film Evaporator (TFE), or Short Path Evaporator (SPE).

The sterols can be further purified. Widely used technologies involve the use of solvents: free sterols are isolated and purified using solvent crystallization and filtration processes.

Many of the processing methods discussed above will result in processes which give sterols in high yields. However, at the same time, the processes are relatively complex, and give rise to undesired side streams and other disadvantages which decrease process profitability and sustainability.

Thus, for example, the saponification method is efficient and produces free sterols in high conversion but causes undesirable processing steps afterwards when fatty acid salts/soaps need to be acidified and separated from its water phase before further evaporations. An acidulation step needs to be performed accurately at a certain pH for conditioning pitch soap for phase separation that is normally carried out by decanting. Acidulation generates high quantities of acidic salty waste water and a middle phase sludge which needs to be treated afterwards.

In processes of the above kind, there is still a high tendency for sterols to be re-esterified back to fatty acid esters after the acidulation step. There are also processing difficulties in sterol separation from saponified residuals due to its hardness in hard pitch fraction.

In some methods sterols are fractionated from a reaction medium in which fatty acid esters are first derivatized to the corresponding fatty acid alcohol esters by using various catalytic transesterification methods. Thus, US2013041192 discloses a method for isolating fatty acid alcohol esters for bio fuels. The method has limited applicability for the production free sterols because free sterols are generally obtained at conversion rates of 50 wt-% or less.

All the above features together lead to expensive and difficult processing which is environmentally unsustainable for today's demands.

The literature also describes processing methods for obtaining sterols from other raw material sources. Such sources are side streams from food fats or feed processing i.e. side streams like deodorizer distillate obtained from refining fats and oils. Many of these methods include traditional processing methods, like extractions and distillations, for obtaining sterol rich phases which can be purified with suitable solvents.

There is therefore a need for new methods which are less complex while still reducing the volume of side streams.

SUMMARY OF THE INVENTION

It is an aim of the present invention to eliminate at least a part of the problems relating to the above technologies.

It is a further aim of the present invention to provide an effective processing method for simultaneous manufacturing of free sterols and fatty acid alcohol esters during the same reaction without using catalysts.

The present invention is based on the concept of recovering sterols from tall oil pitch, which contains steryl esters, by subjecting the tall oil pitch to transefterification with a lower alcohol to provide a reaction mixture containing lower alkyl fatty acid esters, liberated sterols, and at least some unreacted steryl esters;

separating the transesterified esters from the reaction mixture to form a sterol rich fraction which contains unreacted steryl esters, liberating sterols from the unreacted steryl esters and recovering and optionally purifying liberated sterols.

The present invention also allows for the joint production of a first product formed by lower alkyl fatty acid esters and a second product formed by free sterols from tall oil pitch which contains steryl esters.

The present methods can be used for the production of a number of products, for example one or more of food grade sterols having a purity of the sterols of at least 90% by weight, lower alkyl fatty acid ester fractions having a purity of lower alkyl fatty acid esters fraction of at least 40% by weight, and hard pitch residue fractions having a purity of at least 60% by weight of neutral- or unidentified matter.

More specifically, the present processes are characterized by what is stated in the characterizing parts of claims 1 and 24.

The use according to the present invention is characterized by what is stated in claim 26.

Considerable advantages are obtained by the present invention. Effective processing of the raw-material, tall oil pitch, will allow for the recovery of free sterols together with the production of lower alkyl fatty acid esters in a straightforward and sustainable manner. In particular, the present invention provides an effective processing method for manufacturing free sterols and lower alkyl fatty acid esters simultaneously during the same reaction without using catalysts to modify Tall Oil Pitch suitable for isolation of lower alkyl fatty acid esters and/or free sterols.

The recovery of free sterols can be increased to up to 80 wt % or more while avoiding the formation of undesired side streams containing troublesome impurities.

The present products include 1) food grade sterols which have a broad range of applications. The purity of the sterols is generally at least 90% by weight, in particular 95% by weight, preferably about 98% by weight or more. Further products are 2) lower alkyl fatty acid ester fraction for i.e. bio fuel raw material. The purity of lower alkyl fatty acid esters fraction consist in generally at least 40% by weight and preferably more than 50% by weight lower alkyl fatty acid esters. A third group of products is formed by 3) hard pitch residue fractions consisting of 60% or more than 60% by weight of neutral- or unidentified matter and negligible amounts of free sterols, fatty acids, weight lower alkyl fatty acid esters and resin acids. "Negligible amounts" stands for amounts less than about 5% by weight, typically less than 2.5% by weight, in particular less than 1% by weight.

Next, embodiments of the present technology will be examined more closely with the aid of the attached drawings.

DESCRIPTION OF EMBODIMENTS

Figure 1:
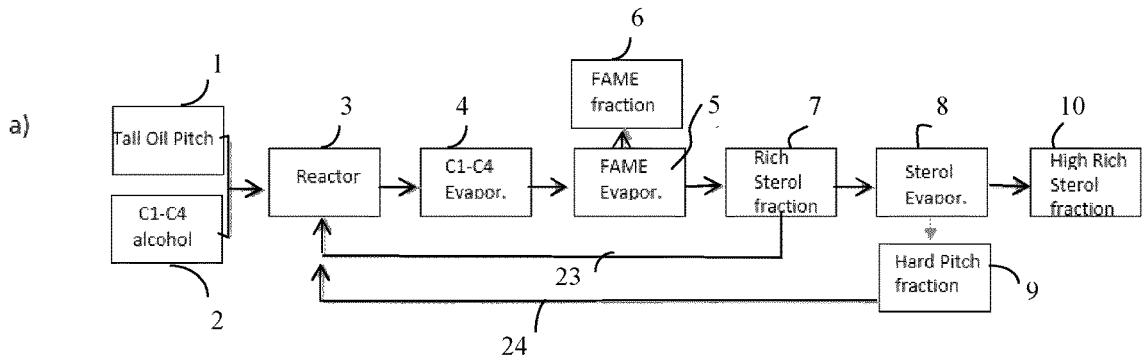
FIG. 1 shows a simplified process scheme of a first embodiment.

As discussed above, the present technology relates to methods of recovering sterols from tall oil pitch which contains steryl esters, comprising a first step of subjecting tall oil pitch to transefterification with a lower alcohol in a reaction zone to provide a reaction product mixture containing lower alkyl fatty acid esters, free sterols and unreacted steryl esters. In a next step, the transesterified esters are separated from the mixture to form a sterol rich residue which contains unreacted steryl esters. Sterols are liberated from the steryl esters of the sterol rich residue, and the free sterols are recovered and optionally purified.

Compared to the method according to US2013041192 for recovering fatty acid alcohol esters for bio fuels, the technology described herein will give, at high yields, free sterols which can be isolated and further purified with known solvent crystallization methods.

In the context of the present invention, "lower alcohols" are in particular aliphatic, linear or branched alcohols having 1 to 5 carbon atoms, for example $C_1$-$C_4$ alcohols. Particular examples are methanol, ethanol, n- and iso-propanol and 1-butanol and mixtures thereof. On typical example is methanol which gives an interesting alkyl ester, fatty acid methyl ester, conventionally abbreviated FAME, which is used as a fuel component for diesel fuels.

"Tall oil pitch" is a non-volatile fraction that is separated at crude tall oil vacuum distillation. Tall oil pitch is the residue after distillation off (under vacuum) of a light phase, a rosin phase, and a fatty acid phase from crude tall oil.

The composition of the tall oil pitch varies depending on the origin of the tall oil and process. Typically, tall oil pitch contains some 30 to 60% by wt of free acids, 20 to 40% by wt of esterified acids, and 10 to 40% by weight of unsaponifiable neutral compounds. More than 50% by wt conventionally consists of high molecular components, about half of which are acidic components. The low molecular free acids are mainly dehydroabietic, abietic, and other resin acids. The esterified acids comprise primarily oleic and linoleic acids. Unsaponifiable fractions are composed of diterpene alcohols, fatty alcohols, sterols, and dehydrated sterols. The alcohol components are essentially present in esterified form.

In the reaction zone, transesterification is carried out by forming a mixture of the starting materials, viz. tall oil pitch, and a lower alcohol or a mixture of lower alcohols.

Optionally a co-solvent, such as a hydrocarbon, or carbon dioxide, or water is added to adjust the viscosity of the reaction mixture, in particular to lower viscosity or to otherwise intensify the reaction, which is subjected to a transesterification reaction in the reaction zone.

In one embodiment, transesterification is carried out in the presence of a catalyst. The catalyst is typically an alkaline agent, such as an alkali metal or earth alkaline metal oxide. Examples of alkaline agents include CaO and MgO.

In another preferred embodiment, transesterification is carried out without a catalyst.

Typically, the transesterification reaction is carried out at a pressure in excess of 50 bar (abs), preferably at a pressure in the range from 60 to 120 bar (abs), and at a temperature 250° C. or more and, in particular, below 300° C., for example at 250-295° C.

In a preferred embodiment, transesterification of tall oil pitch with a lower alcohol is carried out at reaction temperatures below 300° C. to avoid sterol degradation and to obtain high conversion of free sterols and fatty acid lower alcohol esters during the reaction.

The reaction mixture may contain excess alcohol in a concentration of 1-100 wt %, calculated from the mass of the pitch to achieve complete transesterification of the sterols.

Furthermore 0-50 wt % water, calculated from the pitch can be used. Thus, in one embodiment, the transesterification reaction is carried out in an aqueous ambient.

Surprisingly it has been found that moisture of low concentration of water (0.01 to 10%, in particular 0.1 to 5%, calculated from the mass of alcohol) increases the reaction. This is obviously caused by simultaneous hydrolysis during the transesterification reaction and inhibition of reversible esterification between the fatty acids and sterols. As a result an improvement of conversion is obtained. Further, unpurified evaporated alcohol containing small quantities of water after the reaction can be recycled.

Reactions with aqueous alcohol at the conditions discussed above given an increased concentrations of lower alkyl fatty acid esters or synonymously fatty acid alcohol esters and for example reactions with methanol produced fatty acid methyl ester (FAME) and free sterols with relatively low amount of sterol degradation materials.

In one embodiment, the transesterification reaction is carried out in a supercritical or near supercritical state.

At high pressure reactions carried out below a supercritical state, alcohol appears partially in gaseous forms and is accumulated in a gas phase when CSTR type reactors are used. This phenomenon may increase the amount of alcohol needed for the reaction.

Pressure reactors may be equipped with internal or external agitation or agitated by static type mixing elements. In one embodiment, the reaction is carried out without any agitation.

In case of supercritical reactions agitation has a negligible effect on the reaction rate.

Preferably, the weight ratio of virgin tall oil pitch to water is in the range from 100:1 to 20:1.

Typically, in the transesterification reaction, the weight ratio of virgin tall oil pitch to lower alcohol is from 20:1 to 1:1.

In one embodiment, at least 40 mol %, in particular at least 50 mol %, for example at least 55 mol %, of the steryl esters of the tall oil pitch are transesterified during the transesterification step.

After the transesterification reaction, any unreacted lower alcohol and optionally water can be separated from the reaction product mixture.

Thus, the reaction temperature of the reaction mixture can be decreased to allow for evaporation of excess alcohol. Alcohol evaporation can be done in vacuum (pressure lower than normal pressure) by evaporation, such as thin film evaporators, or at excess pressure (pressure higher than normal), for example in pressure flash evaporators or in traditional boiling kettles or similar.

After solvent evaporation lower fatty acid alcohol esters (such as fatty acid methyl esters, FAME) can be evaporated to obtain sterol rich fraction. This evaporation may be carried at reduced pressure and suitable temperature using thin-film-wiped evaporator or falling-film evaporator or similar where fractionation can be performed accurately to avoid free sterol distillation.

In particular, transesterified esters are evaporated off the reaction product mixture at a pressure of less than 50 mbar (abs), in particular less than 10 mbar (abs), preferably 1-5 mbar (abs) and a temperature in the range of 130 to 250° C., depending on the pressure.

In one embodiment, the residue obtained after any separation of unreacted alcohol and of fatty acid alkyl esters, is then subjected to a reaction in which sterols are liberated from the remaining steryl esters.

In one embodiment, free sterols remaining in the reaction product composition are first suitably separated from the sterol rich residue obtained after lower alkyl fatty acid ester separation, and then the remaining fraction concentrated with regard to steryl esters are subjected to a reaction in which sterols are liberated from the remaining steryl esters. The free sterols are recovered from the sterol rich fraction by, for example, evaporation. Thereby a steryl ester residue is obtained which predominantly contains unreacted steryl esters from which further sterol can be obtained.

Preferably not all of the residue is recycled within the same process, i.e. within same processing units assembly. Typically at least a part thereof is removed for example to avoid accumulation of components. Thus, there is normally a split in the flow between fractions 23 and 24 (FIG. 1).

In a first embodiment for liberating sterols from the residue of unreacted steryl esters, at least a part, preferably 10 to 62%, in particular 30 to 62% by weight of the total feed is recycled to the transesterification reaction zone in order to subject unreacted steryl fatty acid esters in the sterol rich fraction to transesterification, optionally together with virgin feed of tall oil pitch.

In a second embodiment for liberating sterols, at least a part, preferably 10 to 62%, in particular 10 to 40% by weight of the of the total feed 1 is recycled to the transesterification reaction zone in order to subject unreacted steryl fatty acid esters in the hard pitch fraction to transesterification, optionally together with virgin feed of tall oil pitch.

As an alternative embodiment to the one described in foregoing, unreacted steryl esters can be conducted to another, e.g. parallel, reaction unit where they can be subjected to transesterification. In such a case, up to 100% of either or both of the above recycled flows can be processed.

In a third embodiment, free sterols are achieved by subjecting a sterol rich fraction and/or hard pitch fraction containing steryl esters to saponification in order to liberate sterols from the steryl esters.

Saponification can be carried out by contacting the sterol rich fraction and/or hard pitch fraction with an alkaline agent. In one embodiment, the sterol rich fraction or the hard pitch fraction is contacted with an alkaline agent selected from the group of alkali metal hydroxides, oxides and carbonates; earth alkaline metal hydroxides, oxides and carbonates, and combinations thereof The alkaline agent is optionally used in the form of an aqueous solution or dispersion.

The alkaline agent can also be selected from alkali metal alkoxides, preferably in the form of a non-aqueous alcoholic solution or dispersion.

The amount of alkaline agent is selected depending on the extent of saponification to be achieved. Typically, saponification is carried out by contacting the sterol rich fraction or hard pitch fraction with a stoichiometric excess of the alkaline agent.

Saponification can be carried out in a continuously operated reaction, for example in continuously stirred tank reactor (CSTR), such as a CSTR pressure reactor, or a tubular reactor.

Saponification is typically continued until at least 75 mol %, in particular at least 85%, suitably at least 95 mol % of the steryl esters have been saponified to yield the corresponding free sterols.

The saponified fraction is dried to remove volatile components. Drying can be carried out by evaporation, in particular using a thin-wiped film evaporator. The evaporation conditions are preferably selected such that negligible amount of foam is formed.

In one embodiment, free sterols are achieved by subjecting a sterol rich fraction and/or hard pitch fraction containing steryl esters to saponification in the above described manner in order to liberate sterols from the steryl esters, or at least a part of the total feed is recycled to the transesterification reaction zone in the above described manner in order to subject unreacted steryl fatty acid esters in the sterol rich fraction and/or in the hard pitch fraction to transesterification, optionally together with virgin feed of tall oil pitch.

Thus, an additional amount of free sterols are achieved by either subjecting a sterol rich fraction and/or hard pitch fraction containing steryl esters to saponification, or by recycling at least a part of the total feed to the transesterification reaction zone.

According to an alternative embodiment, both said saponification and said recycling is carried out in the same overall process scheme.

The recovered sterols are purified by solvent crystallization.

Based on the above, the present technology comprises an embodiment for jointly producing a first product formed by fatty acid lower alkyl esters and a second product formed by high rich sterol fraction formed by free sterols from tall oil pitch which contains negligible concentration of steryl esters, comprising the steps of subjecting the tall oil pitch to a transefterification reaction with a lower alcohol in a reaction zone to provide a reaction product mixture containing fatty acid lower alkyl esters, free sterols, and at least some unreacted steryl esters;

separating the transesterified esters from the reaction product mixture to recover a first product formed by lower alkyl fatty acid esters, and to form a sterol rich fraction which contains free sterols and unreacted steryl esters, liberating sterols from the fractions containing unreacted steryl esters to form further free sterols, and recovering a second product formed by free sterols and optionally purifying said free sterols.

The attached drawings show examples of three illustrative embodiments of the present technology.

A first embodiment comprises combining transesterification in a reaction zone of steryl esters in tall oil pitch, withdrawal of fatty acid alcohol esters, optionally separating free sterols and recycling of unreacted steryl esters to the reaction zone.

An example of this embodiment is shown in FIG. 1, in which the fatty acid alcohol esters are exemplified by fatty acid methyl ester (FAME).

Tall oil pitch raw material 1 and an alcohol reagent 2, for example methanol, are mixed and heated up to a reaction temperature of 250-300° C. at a pressure of 60-200 bar (abs) for a preselected reaction time to achieve reaction between the fatty acids, fatty acid esters and alcohols present in the tall oil pitch. The reaction is carried out in a reactor 3 at near- or supercritical conditions with or without catalysts or water to obtain free sterols and fatty acid alcohol esters.

After the reaction, the reaction effluent is cooled and pressure is lowered. Free, in particular unreacted, alcohol is removed by using pressure or vacuum evaporation methods to obtain solvent free reaction product composition 4. The recovered alcohol may be recycled to the reaction zone (recycle line not shown in the drawing).

Fatty acid alcohol esters 6 are isolated 5. This can be carried out by evaporation or distillation under vacuum with thin-wiped film or short path type evaporator or column type distiller or combined setup i.e. thin film evaporator equipped with a fractionation rectifier column 5 and at a suitable temperature to obtain sterol free alcohol ester fraction. The residue after the evaporation is sterol rich fraction 7, which contains unreacted steryl esters in addition to free sterols.

The sterol rich fraction 7 can be at least partially recycled 23 to the reaction zone 3 where it can be mixed with virgin feed of tall oil pitch and alcohol. The concentration of alcohol may need to be adjusted such that a proper ratio of tall oil pitch to alcohol is reached. Typically, the weight ratio between the total amounts of tall oil pitch to alcohol is about 20:1 to 1:1.

In the example shown in FIG. 1, a part of the sterol rich fraction 7 is recycled and at least a part of free sterols are separated from the fraction 7 and recovered. The high rich sterol fraction can be separated by evaporation 8, for example at high vacuum and elevated temperatures.

Thereby, a high rich sterol product 10 containing the free sterols, and a hard pitch fraction 9 comprising the evaporation residue, are obtained. The latter contains components having lower volatility than the free sterols.

As an example it can be mentioned that the evaporation and distillation units mentioned above can typically be operated at 0.1 to 3 mbar, preferably 0.5 to 1 mbar, and at a temperature of 250 to 310° C., preferably 280 to 295° C.

To increase sterol yields, at least a part of the remaining sterol esters in the hard pitch fraction is esterified by recycling 24 of the fraction into the reaction zone 3 and combined with the virgin feed of tall oil pitch and with potential recycle stream of the previous process step. Further adjustment of alcohol feed is typically carried to out.

The high rich sterol fraction 10 separated and isolated from the rich sterol fraction 8 can be further purified using conventional solvent assisted crystallization methods. Thus, fraction 10 contains typically more than 15 mass % of free sterols along with impurities, such as neutral unsaponifiable materials originating in crude tall oil, small amounts of rosin acids and negligible amounts of fatty acids.

Fraction 10 can be purified for example by dissolving it into an aqueous or non-aqueous solvent mixture comprising solvents, such as 2-butanone, methyl isobuthyl ketone, methyl tert-butyl ketone, ethyl acetate, methanol, ethanol, propanol, butanol, heptane or hexane or mixtures thereof at a first temperature such all material is completely dissolved, crystallizing sterols by decreasing temperature to a second temperature, lower than the first, separating the formed crystals, washing the separated crystals with the same or different solvent or solvent mixture to obtain an impure sterol fraction, dissolving the impure sterol fraction into the same or different solvent as in previous dissolution step and recrystallizing and washing the separated sterol crystals before they are dried to yield sterols in high purity.

Solvents and solvent mixtures used in the foregoing process can be purified and/or recycled as such. For example, impure solvent obtained from a second crystallization step can be entirely or partly used as such as a solvent in a first crystallization without purification to obtain increased sterol yield. Residual material obtained from the solvent recycling may contain increased amount of sterols for partial recycling in any part of the process upstream.

Figure 2:
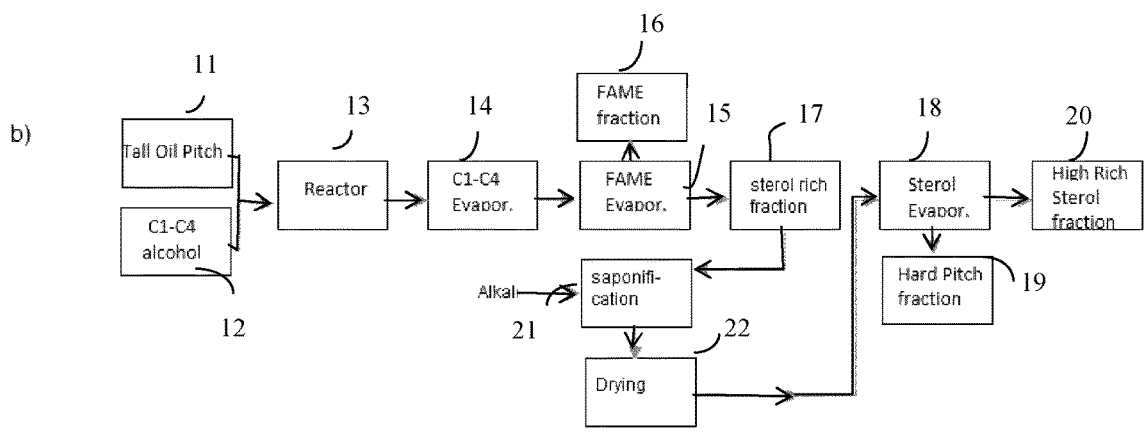
FIG. 2 shows a simplified process scheme of a second embodiment.

A second embodiment comprises combining transesterification in a reaction zone of steryl esters in tall oil pitch, withdrawal of fatty acid alcohol esters, and subjecting unreacted steryl esters to saponification. An example of this embodiment is shown in FIG. 2, in which the fatty acid alcohol esters are exemplified by fatty acid methyl ester (FAME).

Tall oil pitch raw material 11 and an alcohol reagent 12, for example methanol, are mixed and heated up to a reaction temperature of 250-300° C. at a pressure of 60-200 bar (abs) for a preselected reaction time to achieve reaction between the fatty acids, fatty acid esters and alcohols present in the tall oil pitch. The reaction is carried out in a reactor 13 at near- or supercritical conditions with or without catalysts or water to obtain free sterols and fatty acid alcohol esters.

After the reaction, the reaction effluent is cooled and its pressure is reduced. Free, in particular unreacted, alcohol is removed by using pressure or vacuum evaporation methods to obtain solvent free reaction product composition 14. The recovered alcohol may be recycled to the reaction zone (recycle line not shown in the drawing).

Fatty acid alcohol esters 16 are isolated. This can be carried out by evaporation under vacuum with a thin-wiped film or short path type evaporator 15 and at a suitable temperature to obtain sterol free alcohol ester fraction. The residue after the evaporation is a sterol rich fraction 17, which contains unreacted steryl esters in addition to free sterols.

Just as was noted with regard to the embodiment of FIG. 1, the evaporation and distillation units mentioned above can typically be operated at 0.1 to 3 mbar, preferably 0.5 to 1 mbar, and at a temperature of 250 to 310° C., preferably 280 to 295° C.

The sterol rich fraction 17 can be subjected to saponification 21 with an alkali in order to liberate more free sterols from unreacted steryl esters. Compared with conventional tall oil pitch saponification, considerable advantages are obtained. Acidulation of heavy salt containing saponified tall oil pitch can mostly be avoided due to prior removal of fatty acids and alcohol esters before the saponification step.

Saponification can be carried out in a reactor 21, in particular a continuously operated reactor, with a small stoichiometric excess of an alkali solution, such as aqueous NaOH, KOH.— The reaction conditions are preferably selected such that essentially complete saponification of sterol esters is reached. The reactor 21 can be a conventional CSTR pressure reactor or, more efficiently, a tubular continuous reactor.

Saponification generates a small amount of fatty acid salts and water or salts and alcoholic solution which preferably are dried 22 before a subsequent sterol evaporation step 18. This drying step is preferably carried out by evaporation, for example using a thin-wiped film evaporator at conditions which keep foaming negligible.

The dried saponified sterol rich fraction is next subjected to evaporation 18, for example at high vacuum and elevated temperatures. Thereby, a sterol product 20 containing the free sterols, and a hard pitch fraction 19 comprising the evaporation residue, are obtained. The latter contains components having lower volatility than the free sterols.

The high rich sterol fraction 20 separated and isolated from the saponified and dried composition 22 can be further purified using solvent assisted crystallization methods, as explained above in connection with the example of FIG. 1.

Figure 3:
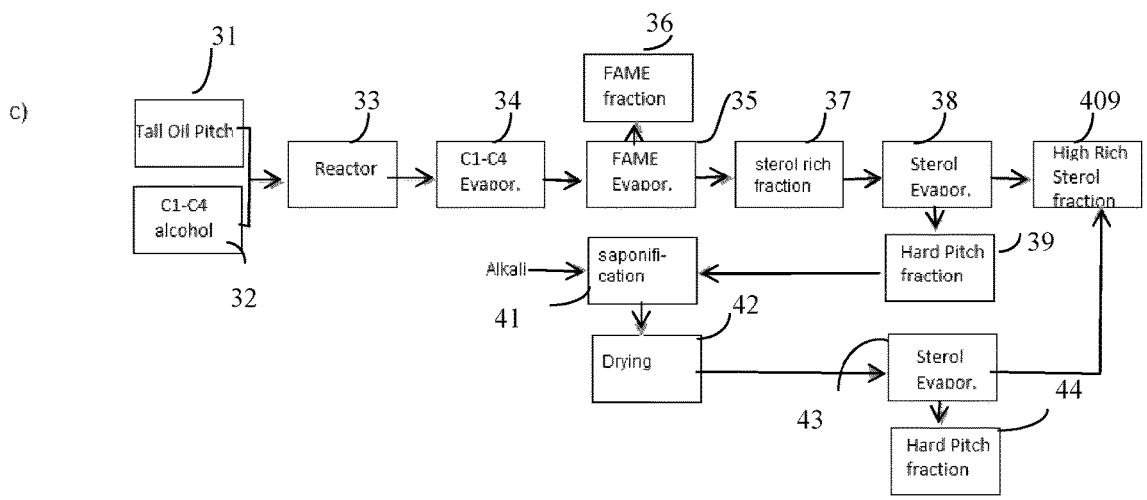
FIG. 3 shows a simplified process scheme of a third embodiment.

A third embodiment comprises combining transesterification in a reaction zone of steryl esters in tall oil pitch, withdrawal of fatty acid alcohol esters, separating free sterols and subjecting unreacted steryl esters to saponification. An example of this embodiment is shown in FIG. 3, in which the fatty acid alcohol esters are exemplified by fatty acid methyl ester (FAME).

Tall oil pitch raw material 31 and an alcohol reagent 32, for example methanol, are mixed and heated up to a reaction temperature of 250-300° C. at a pressure of 60-200 bar (abs) for a preselected reaction time to achieve reaction between the fatty acids, fatty acid esters and alcohols present in the tall oil pitch. The reaction is carried out in a reactor 33 at near- or supercritical conditions with or without catalysts or water to obtain free sterols and fatty acid alcohol esters.

After the reaction, the reaction effluent is cooled and its pressure is reduced. Free, in particular unreacted, alcohol is removed by using pressure or vacuum evaporation methods to obtain solvent free reaction product composition 34. The recovered alcohol may be recycled to the reaction zone (recycle line not shown in the drawing).

Fatty acid alcohol esters 36 are isolated. This can be carried out by evaporation under vacuum with a thin-wiped film or short path type evaporator or similar 35 and at a suitable temperature to obtain sterol free alcohol ester fraction. The residue after the evaporation is a sterol rich fraction 37, which contains unreacted steryl esters in addition to free sterols.

Just as was noted with regard to the embodiment of FIG. 1, the evaporation and distillation units mentioned above can typically be operated at 0.1 to 3 mbar, preferably 0.5 to 1 mbar, and at a temperature of 250 to 310° C., preferably 280 to 295° C.

At least a part of free sterols are separated from the fraction 37 and recovered. The free sterols can be separated by evaporation 38, for example at high vacuum and elevated temperatures. Thereby, a sterol product 40 containing the free sterols, and a hard pitch fraction 39 comprising the evaporation residue, are obtained. The latter contains components having lower volatility than the free sterols.

To increase sterol yields, at least a part of the remaining sterol esters in the hard pitch fraction 39 are subjected to saponification 41 with an alkali in order to liberate more free sterols from unreacted steryl esters.

Similarly to the example of FIG. 2, in the example shown in FIG. 3, saponification can be carried out in a reactor 41, in particular a continuously operated reactor, using a small stoichiometric excess of an alkali solution, such as aqueous NaOH, KOH reagents or similar. The reaction conditions are preferably selected such that essentially complete saponification of sterol esters is reached. The reactor 41 can be a conventional CSTR pressure reactor or, more efficiently, a tubular continuous reactor.

Saponification generates a small amount of fatty acid salts and water or salts and alcoholic solution which preferably are dried 22 before a subsequent sterol evaporation step 18. This drying step is preferably carried out by evaporation, for example using a thin-wiped film evaporator at conditions which keep foaming negligible.

The saponified composition is then dried 42. Drying is preferably carried out by evaporation, for example with a thin-wiped film evaporator while avoiding foaming, as explained above in connection with the example of FIG. 2.

The dried saponified sterol fraction is evaporated 43, for example at high vacuum and elevated temperatures. The evaporated fraction containing free sterol product is typically combined with the sterol product 40. The residue of the evaporation 43 will be a sterol ester free, hard pitch fraction 44 composed of high-boiling components.

The combined sterol fractions 40 can be further purified using solvent assisted crystallization methods, as explained above in connection with the example of FIG. 1.

With reference to all the above disclosed embodiments, it should be pointed out that pressure and temperature greatly affect the concentration of the alkyl ester fraction obtained from the transesterification step. It is preferred to use a moderate vacuum (typically 1-50 mbar) and a low temperature (about 130 to 250° C.) to concentrate rosins and unknown neutral compounds to the volatile fraction and so to increase the purity of sterol rich Fraction. In practice maximal evaporation conditions for FAME recovery should be chosen to enrich maximal amounts of unidentified neutral matter in FAME fraction but avoid evaporation of free sterols. In practice maximal evaporation conditions for high rich sterol fraction should be chosen to enrich maximal amounts of free sterols in high rich sterol fraction but avoid evaporation of unidentified neutral matter in the fraction.

It is also possible to evaporate both the alkyl ester fraction and the sterol rich fraction in a first evaporator and to separate the alkyl ester fraction from the sterol rich fraction in a second evaporator.

The following non-limiting examples are presented by way of illustrations.

EXAMPLES

Example 1

Process for Preparing Free Sterols with Using High or Supercritical Methanolysis without Saponification 722 kg of Tall Oil Pitch (Forchem Oy) and 166 kg of technical grade methanol were heated up to 60° C. and pumped into the tubular reactor with high pressure pump where mixture in rapidly heated up to 280° C. with high pressure of 80 barg. Residence time was 60 min which after reactant was cooled down to 180° C. Excess methanol was partly evaporated by using flash evaporator (GIG Karasek GmbH) and dried entirely with thin film evaporator (GIG Karasek GmbH) at 250° C. under ambient pressure. FAME fraction was recovered by thin film evaporator under 230° C. and 1 mbar, which after high sterol rich fraction and hard pitch fraction was recovered by short path evaporator (GIG Karasek GmbH) at 280° C. (at 0.1 mbar). The products were analyzed by GC.

TABLE 1

|  | Tall oil | Dried reactant | Tall oil pitch after FAME distillation | Evaporated high rich sterol fraction | Hard pitch fraction |
|---|---|---|---|---|---|
| Free sterols | 3 | 7 | 8 | 18 | 0.5 |
| Steryl esters | 16 | 10 | 10 | 1 | 15 |
| Rosin acids | 5 | 4 | 3 | 6 | 0 |
| Fatty acids | 0.5 | 1 | 0.5 | 0.5 | 0 |
| Methyl esters | 0 | 8 | 1.5 | 3 | 0 |
| Grand sterols | 13 | 12 | 14 | 18 | 10 |
| Free sterol conversion-% | — | 29 | — | — | — |
| Mass fraction, kg | 722 | — | 577 | 195 | 382 |
| Sterol yield, kg | 94 | — | 81 | 35 | 38 |

Example 2

Recycling Hard Pitch

Hard pitch obtained from Example 1 were recycled by a reaction as follows:

1033 kg of Tall Oil Pitch (Forchem Oy) and 310 kg of hard pitch fraction and 270 kg of technical grade methanol were heated up to 60° C. and pumped into the tubular reactor with high pressure pump where mixture in rapidly heated up to 280° C. with high pressure of 80 barg. Residence time was 60 min which after reactant was cooled down to 180° C.

Excess methanol was partly evaporated by using flash evaporator (GIG Karasek GmbH) and entirely dried with thin film evaporator (GIG Karasek GmbH) at 240° C. under ambient pressure. FAME fraction was recovered by thin film evaporator under 230° C. and 1 mbar, which after residual pitch was evaporated by short path evaporator (GIG Karasek GmbH) at 280° C. (at 0.1 mbar). The products were analyzed by GC. The results are given in table 2 and 3.

TABLE 2

|  | Tall oil pitch | Hard fraction (recycle) |
|---|---|---|
| Free sterols | 3 | 0.5 |
| Steryl esters | 16 | 15 |
| Rosin acids | 5 | 0 |
| Fatty acids | 0.5 | 0 |
| Methyl esters | 0 | 0 |
| Grand sterols | 13 | 10 |
| Mass fractions, kg | 1033 | 443 |
| Sterol yield, kg | 134 | 44 (178) |

TABLE 3

|  | Dried reactant | Tall oil pitch after FAME distillation | Evaporated high rich sterol fraction | Hard pitch fraction |
|---|---|---|---|---|
| Free sterols | 6.5 | 7.2 | 14.3 | 1 |
| Steryl esters | 7.5 | 11 | 0.5 | 0 |
| Rosin acids | 3.5 | 1.5 | 6 | 0 |
| Fatty acids | 2 | 0.5 | 1 | 0 |
| Methyl esters | 7 | 1.5 | 6.5 | 0 |
| Grand sterols | 11 | 14 | 14.7 | 12 |
| Free sterol conversion-% | 33 | — | — | — |
| Mass fraction, kg | 1476 | 1122 | 428 | 694 |
| Sterol yield, kg | 162 | 157 | 63 | 83 |

The sterol yield was 37% in Example 1 and 47% in Example 2.

As will be apparent, sterol yield was 10% better with circulation process thus recycling improved sterol yield +27%.

Example 3

Saponification

Tall oil pitch (Forchem Oy) was processed by methanolysis as described in Example 1. Free methanol and FAME were removed by distillation to obtain intermediate pitch.

1100 g of intermediate pitch was reacted in closed batch type reactor with 189 g 50-w % KOH in conditions 100→195 deg. Saponified intermediate was cooled and conveyed for drying of excess water into DSL5 thin film evaporator mad by UIC GmbH Germany. Evaporator was equipped with special block wiper peelers. Water was successfully evaporated in conditions 200° C. and 300 mbar vacuum. After drying, intermediate was conveyed to short path evaporator (KDL-5, UIC) where sterol rich fraction was evaporated in conditions 270° C. at a pressure of 0.2 mbar. The products were analyzed by GC and the results are given in table 4.

TABLE 4

| | Tall oil pitch | Dried reactant | Intermediate pitch after FAME distillation | Saponified intermediate | Evaporated sterol rich fraction |
|---|---|---|---|---|---|
| Free sterols | 2.5 | 7 | 8 | 9.5 | 21 |
| Steryl esters | 17 | 9 | 5 | 0 | 0.5 |
| Rosin acids | 4 | 1.5 | 1.5 | 7 (salt) | 1.5 (salt) |
| Fatty acids | 0.5 | 1 | 0.5 | 12 (salt) | 2.7 (salt) |
| Methyl esters | 0 | 8 | 0.5 | 0 | 0.5 |
| Grand sterols | 13 | 12.5 | 11 | 9.5 | 21 |
| Free sterol conversion-% | — | 35 | — | 54 | — |
| Mass fraction, kg | 1375 | — | 1100 | 1195 | 466 |
| Sterol yield, kg | 179 | — | 121 | 114 | 98 |

Sterol yield increased respectively being 4,8% in example-1, 6,1% in example-2 and 8,9% in example-3 when calculated of virgin feed relatively.

INDUSTRIAL APPLICABILITY

The present invention is applicable to the production of sterols which have high purity and which can be broadly used within the food, the pharmaceutical and the chemical industry both as final products and as intermediates for other molecules.

REFERENCE SIGNS LIST 1, 11, 31 tall oil pitch
2, 12, 32 lower alcohol
3, 13, 33 reactor
4, 14, 34 evaporator for lower alcohol
5, 15, 35 fatty acid evaporator
6, 16, 36 fatty acid ester
7, 17, 37 rich sterol residue
8, 18, 38, 43 sterol evaporator
9, 19, 39, 41 pitch residue
10, 20, 40 purified sterol fraction
21, 41 saponification unit
22, 42 dryer
23, 24 recycle line

CITATION LIST

Patent Literature

US2013041192

The invention claimed is:

1. Method of recovering sterols from tall oil pitch which contains steryl esters, comprising the steps of:
   subjecting the tall oil pitch to a transesterification reaction with a lower alcohol in a reaction zone to provide a reaction product mixture containing lower alkyl fatty acid esters, free sterols, and at least some unreacted steryl esters;
   separating the transesterified esters from the reaction product mixture to form a sterol rich fraction which contains free sterols and unreacted steryl esters,
   subjecting at least a part of the sterol rich fraction to saponification in order to liberate sterols from the unreacted steryl esters to form further free sterols, and recovering and optionally purifying the free sterols.

2. The method according to claim 1, wherein the lower alcohol is selected from aliphatic, linear or branched alcohols having 1 to 5 carbon atoms.

3. The method according to claim 1, wherein the transesterification reaction is carried out in supercritical or near supercritical state of the selected alcohol(s) or co-solvent.

4. The method according to claim 1, wherein the transesterification reaction is carried out at a pressure in excess of 50 bar (abs), and at a temperature of 250° C. or more.

5. The method according to claim 1, wherein tall oil pitch is dissolved in a lower alcohol or a mixture of lower alcohols to form a reaction mixture which is subjected to a transesterification reaction in the reaction zone.

6. The method according to claim 1, wherein the transesterification reaction is carried out in an aqueous ambient conditions.

7. The method according to claim 1, wherein the transesterification reaction is carried out at a weight ratio of tall oil pitch to lower alcohol of 20:1 to 1:1.

8. The method according to claim 1, wherein unreacted lower alcohol and optionally water is separated from the reaction product mixture after the transesterification reaction.

9. The method according to claim 1, wherein transesterified esters are separated from the reaction product mixture by evaporation or distillation.

10. The method according to claim 1, wherein free sterols are separated from the sterol rich fraction obtained after separation of transesterified esters from the reaction product mixture so as to yield a hard pitch residue fraction which contains unreacted steryl esters.

11. The method of claim 1, wherein free sterols are recovered from the sterol rich residue by evaporation.

12. The method according to claim 1, wherein at least a part of the feed in total is recycled material to the transesterification reaction zone in order to subject unreacted steryl fatty acid esters in the sterol rich fraction to transesterification, optionally together with virgin feed of tall oil pitch.

13. The method according to claim 1, wherein at least a part of the feed in total is recycled material to the transesterification reaction zone in order to subject unreacted steryl fatty acid esters in the hard pitch fraction to transesterification, optionally together with virgin feed of tall oil pitch.

14. The method according to claim 1, wherein at least a part of the steryl ester fractions is subjected to saponification in order to liberate sterols from unreacted steryl fatty acid esters.

15. The method according to claim 1, wherein saponification is carried out by contacting the sterol rich fraction or the hard pitch residue fraction with an alkaline agent, optionally in the form of an aqueous solution or dispersion.

16. The method according to claim 1, wherein saponification is carried out by contacting the sterol rich fraction or hard pitch residue fraction with a stoichiomeric excess of an alkaline agent.

17. The method according to claim 1, wherein saponification is performed in a CSTR pressure reactor or in a tubular reactor or spinning disc reactor.

18. The method according to claim 1, wherein saponification is continued until at least 75% by weight of the steryl esters have been saponified to yield the corresponding free sterols.

19. The method according to claim 1, comprising drying the saponified residue by evaporation, such that there is no or only negligible foaming.

20. The method according to claim 1, comprising recovering free sterols from the saponified fraction by evaporation.

21. The method according to claim 1, wherein recovered sterols are purified by solvent crystallization.

22. The method according to claim 1, wherein at least 40 mol % of the steryl esters of the tall oil pitch are transesterified.

23. The method according to claim 1 for providing one or more products selected from
- food grade sterols having a purity of the sterols of at least 90% by weight;
- lower alkyl fatty acid ester fractions, having a purity of lower alkyl fatty acid esters fraction of at least 40% by weight; and
- hard pitch residue fraction consisting to more than 60% by weight of neutral- or unidentified matter, and containing minor amounts of free sterols, fatty acids, weight lower alkyl fatty acid esters and resin acids.

24. The method according to claim 1, wherein the lower alcohol is selected from aliphatic, linear or branched $C_1$-$C_4$ alcohols.

25. The method according to claim 1, wherein the transesterification is carried out at a pressure in the range from 60 to 120 bar (abs), and at a temperature of 250° C. or more.

26. The method according to claim 1, wherein the transesterification is carried out at a pressure in excess of 50 bar (abs), and at a temperature of 250-295° C.

27. The method according to claim 1, wherein tall oil pitch is dissolved in a lower alcohol or a mixture of lower alcohols using a co-solvent selected from a hydrocarbon or carbon dioxide.

28. The method according to claim 1, wherein the transesterification reaction is carried out at a weight ratio of tall oil pitch to water of 100:1 to 20:1.

29. The method according to claim 1, wherein transesterified esters are evaporated off the reaction product mixture at a pressure of less than 50 mbar (abs).

30. The method according to claim 1, wherein transesterified esters are evaporated off the reaction product mixture at a pressure of less than 10 mbar (abs).

31. The method according to claim 1, wherein 10 to 62% by weight of the feed in total is recycled material to the transesterification reaction zone in order to subject unreacted steryl fatty acid esters in the sterol rich fraction to transesterification, optionally together with virgin feed of tall oil pitch.

32. The method according to claim 1, wherein 10 to 62% by weight of the feed in total is recycled material to the transesterification reaction zone in order to subject unreacted steryl fatty acid esters in the hard pitch fraction to transesterification, optionally together with virgin feed of tall oil pitch.

33. The method according to claim 1, wherein 10 to 40% by weight of the feed in total is recycled material to the transesterification reaction zone in order to subject unreacted steryl fatty acid esters in the hard pitch fraction to transesterification, optionally together with virgin feed of tall oil pitch.

34. The method according to claim 1, wherein saponification is carried out by contacting the sterol rich fraction or the hard pitch residue fraction with an alkaline agent selected from the group of alkali metal -hydroxides, -oxides and -carbonates or earth alkaline metal -hydroxides, -oxides and -carbonates, and combinations thereof, optionally in the form of an aqueous solution or dispersion, or the alkaline agent is selected from alkali metal alkoxides.

35. The method according to claim 1, wherein saponification is performed in a continuously operated tubular or spinning disc reactor.

36. The method according to claim 1, wherein saponification is continued until at least 85% by weight of the steryl esters have been saponified to yield the corresponding free sterols.

* * * * *